(12) United States Patent
Dimitrova et al.

(10) Patent No.: US 12,404,501 B2
(45) Date of Patent: Sep. 2, 2025

(54) METHOD OF CELL LYSIS

(71) Applicant: EVONIK OPERATIONS GMBH, Essen (DE)

(72) Inventors: Steliyana Dimitrova, Babenhausen (DE); Patrik Stenner, Hanau (DE); Silvia Blank-Shim, Aschaffenburg (DE); Tobias Karl Hubert Müller, Limburg an der Lahn (DE)

(73) Assignee: EVONIK OPERATIONS GMBH, Essen (DE)

( * ) Notice: Subject to any disclaimer, the term of this patent is extended or adjusted under 35 U.S.C. 154(b) by 44 days.

(21) Appl. No.: 18/568,959

(22) PCT Filed: Jun. 2, 2022

(86) PCT No.: PCT/EP2022/065000
§ 371 (c)(1),
(2) Date: Dec. 11, 2023

(87) PCT Pub. No.: WO2022/258470
PCT Pub. Date: Dec. 15, 2022

(65) Prior Publication Data
US 2024/0279592 A1 Aug. 22, 2024

(30) Foreign Application Priority Data
Jun. 11, 2021 (EP) .................................. 21178954

(51) Int. Cl.
*C12N 13/00* (2006.01)
*C12N 1/06* (2006.01)

(52) U.S. Cl.
CPC .............. *C12N 13/00* (2013.01); *C12N 1/063* (2013.01)

(58) Field of Classification Search
CPC .................................. C12N 13/00; C12N 1/063
See application file for complete search history.

(56) References Cited

U.S. PATENT DOCUMENTS

| | | | |
|---|---|---|---|
| 7,246,761 B2 | 7/2007 | Hoppe et al. | |
| 8,138,952 B2 | 3/2012 | Reinhard et al. | |
| 2002/0155611 A1 | 10/2002 | Vernhes et al. | |
| 2004/0097715 A1 | 5/2004 | Teissie et al. | |
| 2014/0326809 A1 | 11/2014 | Müller et al. | |
| 2017/0362564 A1* | 12/2017 | Lamotte | C12N 13/00 |
| 2018/0163167 A1 | 6/2018 | Minamitani et al. | |

FOREIGN PATENT DOCUMENTS

| | | |
|---|---|---|
| CA | 2680667 A1 | 9/2008 |
| CN | 103951728 A | 7/2014 |
| JP | 2021045071 A | 3/2021 |
| WO | 2016194782 A1 | 12/2016 |

OTHER PUBLICATIONS

Borodinas, S et al. Algae cell wall disruption by electrohydraulic shock. Journal of Vibroengineering. 2016. 18(4): 2508-2514. (Year: 2016).*
Coleman, AJ et al. The spatial distribution of cavitation induced acoustic emission, sonoluminescence and cell lysis in the field of a shock wave lithotripter. Phys. Med. Biol. 1993. 38: 1545-1560. (Year: 1993).*
International Search report PCT/EP2022/065000 dated Sep. 8, 2022 (pp. 1-48).
Search report in corresponding EP 21178954.0 dated Dec. 8, 2021 (pp. 1-68).
Muharram Mmabdel-Kader MS: "Utilization of gel electrophoreses for the quantitative estimation of digestive enzyme papain", Saudi Pharm J., vol. 25, No. 3, 2017, pp. 359-364, XP029945120, DOI: 10.1016/j.jsps.2016.09.002.

* cited by examiner

*Primary Examiner* — David W Berke-Schlessel
*Assistant Examiner* — Susan E. Fernandez
(74) *Attorney, Agent, or Firm* — Millen, White, Zelano & Branigan; Ryan R. Pool

(57) ABSTRACT

The invention relates to a method of cell lysis for forming at least one pore in the cell wall and/or cell membrane of a cell in an aqueous medium for release of at least one intracellular target protein and/or lipid from the cell into the aqueous medium, including subjecting the cell with the intracellular target protein and/or lipid in the aqueous medium to an electrohydraulic comminution; and separating the target protein and/or lipid from the cell.

The electrohydraulic comminution is brought about by a pulse current source. The cell in the aqueous medium is subjected to electrical impulse discharges between at least two electrodes of an underwater radio path of a container at a specific operating voltage, impulse energy, and pulse frequency, and at least one pore is formed in the cell wall and/or cell membrane.

15 Claims, 1 Drawing Sheet

METHOD OF CELL LYSIS

FIELD OF THE INVENTION

The present invention relates to a new method of cell lysis that enables the extraction of proteins and lipids from cells. In particular, the new method of cell fragmentation comprises using electrohydraulic fragmentation, also known as shock therapy to fractionate the cell to extract the proteins and/or lipids within the cells.

BACKGROUND OF THE INVENTION

Many biological products such as proteins and lipids are usually produced intracellularly and the cells must be lysed to obtain them. Established methods for cell lysis are mechanical in nature such as grinding in ball mills and high-pressure homogenization.

The ball mill is one of the most effective methods for disrupting cells. The effectiveness of this method depends on several parameters: vibration frequency, digestion time, number of passes, cell density, geometry of the grinding chamber as well as composition and packing density, size and weight of the balls used. It is also well known that the high efficiency of the process (i.e. maximum target product extracted from the cell) is a result of the complete destruction of the cell wall caused by the collision and friction of the balls.

Mechanical cell disruption in high pressure homogenizers is also effective. In this method, the cell suspension is conveyed through an opening valve using high pressure. The disruption of the cells and thus the release of the intracellular components is caused by the high shear force on the opening valve. There are also several parameters there that affect the effectiveness of this method. For example, the working pressure, the geometry of the valve, the cell density and the temperature have to be varied to adapt to the different cells.

These methods of cell disruption may be efficient, but they have certain disadvantages. The mechanical energy introduced during the digestion, which is converted by friction (i.e. impact of the balls, conveyance through the opening valve, etc.), causes the sample to be heated and this heat may result in the destruction of the target protein and/or lipid. Further, both these known methods result in the complete destruction of the cell wall and the cell membrane thus releasing further intracellular components including cell debris of varying sizes, which makes mechanical lysis less selective. The subsequent step of separating the desired target products from the unwanted components is also labour and cost intensive. In particular, these downstream processing steps are time-intensive, and make up to 75% of the production costs. As cell lysis as an early process step, it has a high impact on the remaining purification steps. The higher the requirement for product purity (especially for drugs), the more cleaning steps are required, so the product yield can be decreased by up to 80%. In order to reduce the number of purification steps after the cell lysis and to minimize the loss of product yield, there is a need in the art for a way to release the product without destroying the cell membrane into small fragments.

In particular, there is a need in the art for a cell disruption method that provides a means of obtaining the target proteins and/or lipids of the required purity with as few downstream steps as possible (i.e. target protein recovery, concentration, purification and packaging) thus saving costs and improving the quality of the product for it is known that with every step that the target product goes through, there is a risk of the biological activity and stability of the product being impaired.

DESCRIPTION OF THE INVENTION

Figure 1:
FIG. 1 is an overview of the method of cell lysis according to any aspect of the present invention where electrohydraulic comminution is used in cell lysis.

The present invention attempts to solve the problems above by providing a method that overcomes the disadvantages of mechanical and chemical cell lysis and to facilitate the separation of the product from other undesirable cell components such as cell debris. In particular, the method is an electrochemical lysis in which pores are formed and proteins and/or lipids are released from the inside of the cell without the cell wall being broken up into many small fragments. This is particularly advantageous as since the cell membrane's form and size remain due to the formation of pores through which the intracellular target products are released from the cell, separation of the cell mass from the product is also made easier. FIG. 1 provides an overview of the method of cell lysis according to any aspect of the present invention.

According to one aspect of the present invention, there is provided a method of cell lysis for forming a plurality of pores in the cell wall and/or cell membrane of a cell in an aqueous medium for release of at least one intracellular target protein and/or lipid from the cell into the aqueous medium, the method comprising:

(a) subjecting the cell with the intracellular target protein and/or lipid in the aqueous medium to an electrohydraulic comminution; and (b) separating the target protein and/or lipid from the cell, wherein the electrohydraulic comminution is brought about by means of a pulse current source, the cell in the aqueous medium is subjected to electrical impulse discharges between at least two electrodes of an underwater radio path of a container at an operating voltage in the range from 40-130 kV, an impulse energy of 50 to 1500 J per electrode, a pulse frequency of 1 Hz for 40-1000 second, whereby at least one pore is formed in the cell wall and/or cell membrane.

Electrohydraulic comminution or electrohydraulic fragmentation (EHF) is a shockwave-based technology that is currently being used for recycling of batteries and related products. In this technology, target material is first surrounded by an aqueous medium with low conductivity. At least two electrodes are introduced into the aqueous medium and shockwaves are generated using a high-voltage pulse generator. The shockwaves pass through the target material and break it down into small fragments from the mechanical weak points or interface of metal and non-metals. It was therefore particularly surprising that EHF could be effectively used for cell lysis. This was unexpected as EHF was never used in the field of biology, biotechnology and/or bioprocessing in combination with cells. Further, using electrohydraulic fragmentation according to any aspect of the present invention in cell lysis enables a greater distance between the two electrodes (i.e. cathode and anode) to be present compared to other electric impulse methods used in the state of the art. The greater distance between the two electrodes is at least about 20 cm or more. This distance between the two electrodes provides a sufficient field intensity to bring about cell lysis without having a negative effect on the product yield.

According to any aspect of the present invention, electrohydraulic comminution may be used for cell lysis. The term "cells" as used herein refers to biological cells, i.e. prokaryotic and eukaryotic cells. These can be mammalian cells (such as, for example, cells from man), plant cells or microorganisms such as yeasts, fungi or bacteria. Cells may also include viruses. Prokaryotic cells include gram-negative and gram-positive bacteria and eukaryotic cells include plant cells, fungal cells and animal cells. In particular, the cell according to any aspect of the present invention refers to yeast cell, bacterial cell and/or plant cell.

Suitable bacteria, yeasts or fungi are in particular those bacteria, yeasts or fungi that are deposited in the Deutsche Sammlung von Mikroorganismen und Zellkulturen (German Collection of Microorganisms and Cell Cultures) GmbH (DSMZ), Brunswick, Germany, as bacterial, yeast or fungal strains.

In particular, the cells may be selected from the genera *Aspergillus, Corynebacterium, Brevibacterium, Bacillus, Acinetobacter, Alcaligenes, Lactobacillus, Paracoccus, Lactococcus, Candida, Pichia, Hansenula, Kluyveromyces, Saccharomyces, Escherichia, Zymomonas, Yarrowia, Methylobacterium, Ralstonia, Pseudomonas, Rhodospirillum, Rhodobacter, Burkholderia, Clostridium* and *Cupriavidus*. More in particular, the cells may be selected from the group consisting of *Aspergillus nidulans, Aspergillus niger, Alcaligenes latus, Bacillus megaterium, Bacillus subtilis, Brevibacterium flavum, Brevibacterium lactofermentum, Burkholderia andropogonis, B. brasilensis, B. caledonica, B. caribensis, B. caryophylli, B. fungorum, B. gladioli, B. glathei, B. glumae, B. graminis, B. hospita, B. kururiensis, B. phenazinium, B. phymatum, B. phytofirmans, B. plantarii, B. sacchari, B. singaporensis, B. sordidicola, B. terricola, B. tropica, B. tuberum, B. ubonensis, B. unamae, B. xenovorans, B. anthina, B. pyrrocinia, B. thailandensis, Candida blankii, Candida rugosa, Corynebacterium glutamicum, Corynebacterium efficiens, Escherichia coli, Hansenula polymorpha, Kluveromyces lactis, Methylobacterium extorquens, Paracoccus versutus, Pseudomonas argentinensis, P. borbori, P. citronellolis, P. flavescens, P. mendocina, P. nitroreducens, P. oleovorans, P. pseudoalcaligenes, P. resinovorans, P. straminea, P. aurantiaca, P. aureofaciens, P. chlororaphis, P. fragi, P. lundensis, P. taetrolens, P. antarctica, P. azotoformans, 'P. blatchfordae', P. brassicacearum, P. brenneri, P. cedrina, P. corrugata, P. fluorescens, P. gessardii, P. libanensis, P. mandelii, P. marginalis, P. mediterranea, P. meridiana, P. migulae, P. mucidolens, P. orientalis, P. panacis, P. proteolytica, P. rhodesiae, P. synxantha, P. thivervalensis, P. tolaasii, P. veronii, P. denitrificans, P. pertucinogena, P. cremoricolorata, P. fulva, P. monteilii, P. mosselii, P. parafulva, P. putida, P. balearica, P. stutzeri, P. amygdali, P. avellanae, P. caricapapayae, P. cichorii, P. coronafaciens, P. ficuserectae, 'P. helianthi', P. meliae, P. savastanoi, P. syringae, P. tomato, P. viridiflava, P. abietaniphila, P. acidophila, P. agarici, P. alcaliphila, P. alkanolytica, P. amyloderamosa, P. asplenii, P. azotifigens, P. cannabina, P. coenobios, P. congelans, P. costantinii, P. cruciviae, P. delhiensis, P. excibis, P. extremorientalis, P. frederiksbergensis, P. fuscovaginae, P. gelidicola, P. grimontii, P. indica, P. jessenii, P. jinjuensis, P. kilonensis, P. knackmussii, P. koreensis, P. lini, P. lutea, P. moraviensis, P. otitidis, P. pachastrellae, P. palleroniana, P. papaveris, P. peli, P. perolens, P. poae, P. pohangensis, P. psychrophila, P. psychrotolerans, P. rathonis, P. reptilivora, P. resiniphila, P. rhizosphaerae, P. rubescens, P. salomonii, P. segitis, P. septica, P. simiae, P. suis, P. thermotolerans, P. aeruginosa, P. tremae, P. trivialis, P. turbinellae, P. tuticorinensis, P. umsongensis, P. vancouverensis, P. vranovensis, P. xanthomarina, Ralstonia eutropha, Rhodospirillum rubrum, Rhodobacter sphaeroides, Saccharomyces cerevisiae, Yarrowia lipolytica* and *Zymomonas mobile*. More in particular, the cell may be a bacterial cell selected from the group consisting of *Pseudomonas, Corynebacterium, Bacillus* and *Escherichia*. Even more in particular, the cells may be selected from the group consisting of *Pseudomonas putida, Escherichia coli* and *Burkholderia thailandensis*.

More in particular, the cell may be a yeast cell. The yeast cell according to any aspect of the present invention may be selected from the group consisting of *Candida, Yarrowia, Pichia, Torulopsis, Rhodotorula, Saccharomyces,* and *Wickerhamiella*. In particular, the yeast cell may be selected from the group consisting of *Candida tropicalis, Candida cloacae, Yarrowia lipolytica, Schizosaccharomyces pombe, Rhodotorula glutinis, Wickerhamiella domercqiae, Pichia pastoris, Saccharomyces cerevisiae* and the like. More in particular, the yeast cell may be *Pichia pastoris* or *Saccharomyces cerevisiae*.

All the above-mentioned cells excluding viruses, which have a protein capsid, have a plasma membrane, i.e. protein-lipid bilayer that forms a barrier separating cell contents from the extracellular environment. Plant cells, prokaryotic cells, algae and fungus cells further have a cell wall which provides physical support. Bacterial cell walls are made up of peptidoglycan and yeast cell walls of two layers of β-glucan. Both the bacterial and the yeast cell walls are further surrounded by an outer glycoprotein layer rich in mannan, a carbohydrate. Plant cell walls are made up of multiple layers of cellulose. According to any aspect of the present invention, the phrase 'cell wall and/or cell membrane' covers all the layers that separate the intracellular environment of the cell from the external environment of the cell.

The term "cell lysis" as used herein refers to a disruption of one of many cells such that the cells' outer layer is permanently or temporarily disrupted to release their contents for further analysis, modification, or use. In particular, to analyse cell contents, as for example the genome (DNA contents), the proteome (protein contents), the methylom (DNA methylation patterns) or the transcriptome (RNA contents), as well as intracellular structures, like organelles, the cytoskeleton and so forth, the cells have to be disrupted, i.e. their capsid, cell membranes and/or cell walls have to be disrupted. It is expected that the more rigid the outer cell structures, i.e. capsid, cell membranes and/or cell walls are, the more difficult it is to disrupt them. In particular, cell lysis may be a temporary disruption of the cell wall and/or membrane such that the contents within the cell can be released to the external environment without the cell wall and/or membrane being permanently destroyed. More in particular, the temporary cell disruption or cell lysis may comprise the formation of at least one pore in the cell membrane and/or cell wall of the cell when the cell is in an aqueous medium and is subject to electrohydraulic comminution. This temporary cell disruption, a result of the method of cell lysis according to any aspect of the present invention may result in the formation of at least one pore in the cell membrane and/or cell wall. The pore(s) are a passage for the intracellular target proteins and/or lipids to exit the cell into the aqueous medium surrounding the cell.

The term "cell wall" as used herein refers to an outer layer that surrounds certain cell types, namely plants, yeast, fungi, algae, and certain prokaryotes. In one example, the term refers to a tough or rigid layer that surrounds the plasma membrane and provides support to the cell. In another example, the cell wall may be made up of a number of components including but not limited to cellulose, hemicellulose, pectin, peptidoglycan, glucosamine, chitin, glycoprotein, and/or polysaccharide.

The term "cell membrane" as used herein in the broadest sense, refers generically to the boundary membrane, external membrane, interfacial membrane or protoplasmic membrane that separates the protoplasm of the cell from the outside layer and/or from the cell wall. The cell membrane may be a lipid bilayer.

The phrase 'plurality of pores' refers to more than one pore. The cell wall and/or cell wall according to any aspect of the present invention may comprise a plurality of pores (i.e. more than one pore).

The term "pore" as used herein refers to an opening, which may include a hole, tear, cavity, aperture, break, gap, or perforation within the cell membrane and/or cell wall depending on what is present in the target cell used in the method according to any aspect of the present invention. In one example, the cell may be a plant cell and the pore formed, using the method according to any aspect of the presence invention, may be a cavity through the cell wall and cell membrane of the plant cell wherein the cavity has a diameter large enough for the target protein and/or lipid to be released from within the plant cell out to the surrounding aqueous medium. In another example, the cell may be a yeast cell and when the yeast cell is subjected to electrohydraulic comminution, a pore may be formed in the cell membrane and the cell wall with two layers of β-glucan, forming a passage for the target protein(s) and/or lipid(s) to be released from the inside of the cell to the surrounding aqueous medium. The pore(s) may have a size sufficient to be a passageway through the cell membrane and/or cell wall for transport of proteins and/or lipids that have a molecular weight between 20 kDa and 120 kDa. In particular, the pore may be big enough to allow proteins with molecular weight between 20 kD to 120 kDa to be released from within the cell. More in particular, the pore may be large enough to allow proteins with molecular weight between 20 kDa to 110 kDa, 20 kDa to 100 kDa, 20 kDa to 90 kDa, 20 kDa to 80 kDa, 20 kDa to 70 kDa, 25 kDa to 120 kDa, 25 kDa to 110 kDa, 25 kDa to 100 kDa, 25 kDa to 90 kDa, 25 kDa to 80 kDa, 25 kDa to 70 kDa, 30 kDa to 120 kDa, 30 kDa to 110 kDa, 30 kDa to 100 kDa, 30 kDa to 90 kDa or 30 kDa to 80 kDa to pass through.

According to yet another aspect of the present invention, each pore may comprise an average diameter between 5 to 40 nm. It is to be understood that the term pore does not put any geometric limitation on the nature of the pores which may be of regular or irregular morphology. It should also be recognized that not all pores may be of the same diameter. The term 'average diameter' as used herein refers to a diameter length that is not expected to be the same in every pore. The 'average diameter' refers to the diameter of a pore which in some way represents the plurality of pores or the total number of pores. The average diameter of the pore according to any aspect of the present invention may be between 1 to 50 nm. In particular, the average diameter of the pore may be between 5 to 50, 10 to 50, 15 to 50, 20 to 50, 25 to 50, 30 to 50, 1 to 45, 5 to 45, 10 to 45, 15 to 45, 20 to 45, 25 to 45, 1 to 40, 5 to 40, 10 to 40, 15 to 40, 20 to 40, 25 to 40, 1 to 35, 5 to 35, 10 to 35, 15 to 35, 20 to 35, 25 to 35 and the like. More in particular, the average diameter of the pore may be about 5, 10, 15, 20, 25, 30, 35, 40, 45 or 50 nm.

In one example, the pore is formed within the cell membrane of the cell and in another example, the pore is in the cell wall and cell membrane of the cell. The pore(s) may be formed on about 75%, 70%, 65%, 60%, 55%, 50%, 45%, 40%, 35% or 30% of the cell membrane and/or cell wall surface. This may be measured using any method known in the art. In one example, confocal laser scanning microscopy may be used to estimate the percentage of the membrane and/or cell wall covered by pores. The plurality of pores may only be temporarily present in the cell membrane and/or cell wall. In particular, the plurality of pores may appear when the cell according to any aspect of the present invention is subject to an electrohydraulic comminution and the plurality of pores in the cell may cease to exist when the electrohydraulic comminution is removed. It is understandable that there will be a first latent between the time the cell is subjected to electrohydraulic comminution and the time the first pore appears in the cell membrane and/or cell wall and a second latent between the time the cell is no longer subjected to electrohydraulic comminution and the time the last pore disappears in the cell membrane and/or cell wall.

The cell according to any aspect of the present invention may be present in an aqueous medium. The aqueous medium may be any liquid with a conductivity of ≤400 μS/cm. Any conductometer may be used to measure the conductivity of the liquid. In particular, the conductometer may be in the form of a conductivity sensor or meter. In particular, aqueous medium may be any liquid with a conductivity of ≤350, 300, 250, 200, 150, 100, 90, 80, 75, 70 μS/cm. The aqueous medium may be selected from the group consisting of water, oils, surfactants, acids, bases, oxidizing agents and mixtures thereof. More in particular, the aqueous medium may be distilled water. The container in which the method of cell lysis according to any aspect of the present invention takes place may be able to hold from 1 to 300 l of the aqueous medium. More in particular, the volume of aqueous medium in the container may be about 100, 90, 80, 70, 60, 50, 40, 30, 25, 20, 15, 10, 5 l. The term 'about' as used herein refers to a variation within 20 percent. In particular, the term "about" as used herein refers to +/−20%, more in particular, +/−10%, even more in particular, +/−5% of a given measurement or value.

The term "target protein and/or lipid" as used herein refers to the protein and/or lipid whose expression in a cell is of interest. According to any aspect of the present invention, the target protein and/or lipid from the cell that may be released into the aqueous medium, may be produced naturally in the cell. In another example, the cell may be genetically modified to produce the target protein and/or lipid within the cell. The resultant target protein and/or lipid may be referred to as a heterologous target protein and/or lipid. In particular, the term "heterologous target protein and/or lipid" refers to a recombinant protein and/or lipid that is not normally expressed by the host cell, tissue, or species. The use of the term 'target protein and/or lipid' according to any aspect of the present invention includes heterologous target protein and/or lipid. The target protein and/or lipid may have a molecular weight between 20 kDa and 120 kDa. In particular, the target protein and/or lipid may have a molecular weight between 20 kDa to 110 kDa, 20 kDa to 100 kDa, 20 kDa to 90 kDa, 20 kDa to 80 kDa, 20 kDa to 70 kDa, 25 kDa to 120 kDa, 25 kDa to 110 kDa, 25 kDa to 100 kDa, 25 kDa to 90 kDa, 25 kDa to 80 kDa, 25 kDa to 70 kDa, 30 kDa to 120 kDa, 30 kDa to 110 kDa, 30 kDa to 100 kDa, 30 kDa to 90 kDa or 30 kDa to 80 kDa. More in particular, the target protein may have a molecular weight between 20 kDa to 110 kDa, 20 kDa to 100 kDa, 20 kDa to 90 kDa, 20 kDa to 80 kDa, 20 kDa to 70 kDa, 25 kDa to 120 kDa, 25 kDa to 110 kDa, 25 kDa to 100 kDa, 25 kDa to 90 kDa, 25 kDa to 80 kDa, 25 kDa to 70 kDa, 30 kDa to 120 kDa, 30 kDa to 110 kDa, 30 kDa to 100 kDa, 30 kDa to 90 kDa or 30 kDa to 80 kDa. The target lipid may have a molecular weight between 20 kDa to 110 kDa, 20 kDa to 100 kDa, 20 kDa to 90 kDa, 20 kDa to 80 kDa, 20 kDa to 70 kDa, 25 kDa to 120 kDa, 25 kDa to 110 kDa, 25 kDa to 100 kDa, 25 kDa to 90 kDa, 25 kDa to 80 kDa, 25 kDa to 70 kDa, 30 kDa to 120 kDa, 30 kDa to 110 kDa, 30 kDa to 100 kDa, 30 kDa to 90 kDa or 30 kDa to 80 kDa. More in particular, the target lipid may have a molecular weight between 30 kDa to 85 kDa. Even more in particular, the target lipid may be from *Saccharomyces cerevisiae* and may have a molecular weight between 31 kDa to 84 kDa. Examples of target lipids according to any aspect of the present invention may be sterols (as lanosterol, squalene, zymosterol etc), phospholipids, fatty acids and the like A skilled person would understand that in the method according to any aspect of the present invention, the target protein and/or lipid released from the cell will be released together with other proteins and/or lipids. In particular, the cell lysate product released after step (a) of the method according to any aspect of the present invention may be enriched in the target protein and/or lipid but may also contain other components. Examples of such other components include, but are not limited to, proteins normally expressed by the host cell or tissue, cellular debris, and cell broth for example. The term 'cell lysate product' refers to the resultant elements that are released from the cell into the aqueous medium after step (a) of the cell lysis method according to any aspect of the present invention. The cell lysate product comprises other components as defined above in combination with the target protein and/or lipid.

The step (b) of separating the target protein and/or lipid from the cell, according to any aspect of the present invention, involves separating the other components from the released target protein and/or lipid. Since, the cell lysis method according to any aspect of the present invention does not involve the complete destruction of the cell wall and/or membrane, there may not be too much unwanted material in the cell lysate product after step (a). Any known technique of separation may be used to separate the target protein and/or lipid from the other components. Examples of such techniques include, but are not limited to, size exclusion chromatography, hydrophobic interaction chromatography, ion exchange chromatography, free-flow-electrophoresis, affinity chromatography, HPLC, lyophilization, extraction, filtration and centrifugation, sieving, filtering, washing, centrifugation, microfiltration, packed bed chromatography ("PBC"), expanded bed chromatography ("EBC"), or other types of column chromatography, for example. The step of "separating the target protein and/or lipid from the cell" does not require a complete separation of all the other components. Since the cells used according to any aspect of the present invention is subjected in step (a) to EHF and post EHF treatment, not all the cells would have been destroyed, the cell lysis method according to any aspect of the present invention may be beneficial for the following downstream processing in step (b) (i.e. centrifugation and filtration). In particular, due to the remaining cell form and size after the EHF treatment (i.e. step (a)) the electrically lysed cells can be easily separated from the target protein and/or lipid (step (b)). Since the number of purification steps can be reduced, the downstream processing is made easier, faster and less cost intensive.

Centrifugation may be used to separate the target protein and/or lipid from the cell. Any type of centrifugation process can be used. Specific parameters of the centrifugation would depend, at least in part, on factors such as the nature of the target protein (amino acid sequence and charge, for example) and/or lipid, and the nature of the host cell expressing the target protein. One example of a centrifugation process that can be used is a continuous disk stack centrifuge. In another example, EBC may be used to separate the target protein and/or lipid from the cell. EBC is a single pass operation in which desired proteins are purified from crude, particulate containing solution without the need for clarification, initial purification, or concentration. Although not necessary, EBC can be utilized with prior clarification, purification, or concentration steps, such as centrifugation, microfiltration, or the like. EBC utilizes an adsorbent bed that is suspended in an equilibrium caused by the balance between particle sedimentation velocity and upward liquid flow velocity. The adsorbent expands in the bed and creates a distance between the adsorbent particles (this distance corresponds to the void volume as that term is used in chromatography techniques), that allows for relatively unhindered passage of cells, cell debris, and other particulates that may be present in the aqueous medium. Specific parameters of a useful protocol would depend, at least in part, on the nature of the target protein to be separated, the host cells from which it is being separated, and other such factors.

Figure 2:
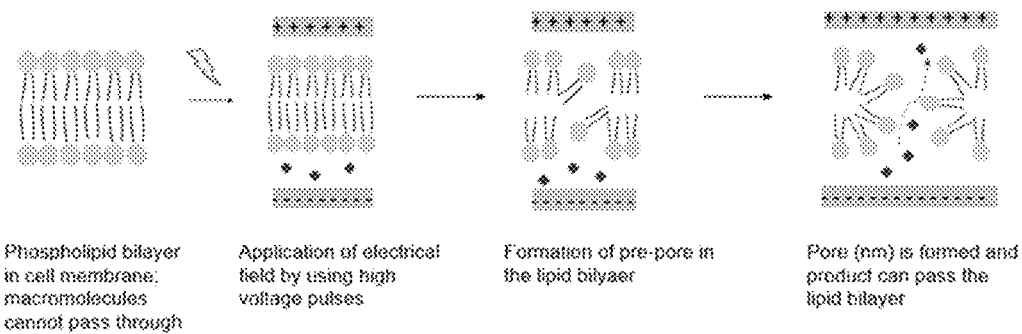
FIG. 2 shows the series of events that take place within the cell membrane to form a pore in the cell membrane.
Figure 3:
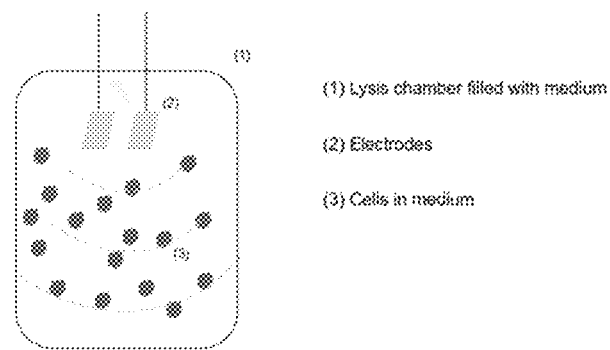
FIG. 3 is a picture of a lysis chamber filled with aqueous medium where the cells in the medium are subjected to electrohydraulic comminution in the presence of at least two electrodes. The dotted line shows the coverage of the shock waves that radiate from the electrodes within the aqueous medium.

EHF uses mechanical shock waves, which are generated in the aqueous medium to bring about an energy coupling that results in a separation of the components of the cell wall and/or cell membrane resulting in the formation of at least one pore or a plurality of pores. The shock waves are generated using the electro-hydraulic effect, where a short-term, intense arc is started in the aqueous medium between at least two electrodes as part of an electrode system. There are also pulse capacitors used which are charged to an operating voltage and connected to the electrode system in a container filled with an aqueous medium with the aid of a spark gap. FIG. 3 shows how EHF can be used to result in cell lysis. US20140326809, U.S. Pat. No. 7,246,761B2 and CA2680667A1 disclose suitable means of producing EHF that may be used in the method according to any aspect of the present invention. In particular, the operating voltage is 40 kV-130 kV and the pulse frequency is 1 Hz. The EHF duration may be varied depending on the material (i.e. the cell and how thick the cell membrane and/or cell wall is). By generating shock waves a parallel electric field is applied which can be used for selective cell lysis. The resting membrane potential prevails on the cell membrane, which ranges from −50 to −200 mV depending on the cell type. If the cell is exposed to an electric field, the resting membrane potential is changed and thus homeostasis is lost. The change in membrane stability means that the phospholipids can now tilt. The cell membrane does not tear but forms a pre-pore. The reorientation of the phospholipids continues until the actual pore in the lipid bilayer is formed, so macromolecules (target protein and/or lipid) can penetrate through the bilayer from the inside to the outside of the cell. This is shown in FIG. 2.

An advantage of the method according to any aspect of the present invention is that the distance between the electrodes doesn't affect the success of the cell lysis process. Due to the presence of the shock waves, the electric field is spread through the entire aqueous medium evenly, so that all cells can be lysed independent of their distance from the electrodes. In order to achieve an optimal cell lysis the operating voltage may be within the range of 40-150 kV. In particular, the operating voltage may be within the range of 40-140, 40-130, 40-120, 40-110, 40-100, 50-150, 50-140, 50-130, 50-120, 50-110, 50-100, 60-150, 60-140, 60-130, 60-120, 60-110, 60-100 kV and the like. More in particular, the operating voltage may be about 40, 50, 60, 70, 80, 90, 100, 110, 120, 130, 140, or 150 kV. In order to achieve an optimal cell lysis together with the operating voltage, the number of pulses present in the aqueous medium may be between 40 and 1000 with a frequency of 1 Hz. In particular, the number of pulses may be 40-900, 40-800, 40-700, 40-600, 40-500, 40-400, 40-300, 40-200, 40-100, 50-1000, 50-900, 50-800, 50-700, 50-600, 50-500, 50-400, 50-300, 50-200, 50-100, 60-1000, 60-900, 60-800, 60-700, 60-600, 60-500, 60-400, 60-300, 60-200, 60-100, 70-1000, 70-900, 70-800, 70-700, 70-600, 70-500, 70-400, 70-300, 70-200, 70-100, 80-1000, 80-900, 80-800, 80-700, 80-600, 80-500, 80-400, 80-300, 80-200, 80-100, 90-1000, 90-900, 90-800, 90-700, 90-600, 90-500, 90-400, 90-300, 90-200, 100-1000, 100-900, 100-800, 100-700, 100-600, or 100-500 at a frequency of 1 Hz. Since the pulse frequency for optimal cell lysis according to any aspect of the present invention may be 1 Hz, the number of pulses may refer to the number of seconds that the cell in the aqueous medium may be subjected to EHF.

In one example, to achieve an optimal cell lysis, the operating voltage is about 40 kV, the pulse frequency is 1 Hz and the pulse was applied for 1000 seconds. In another example, the operating voltage is about 130 kV, the pulse frequency is 1 Hz and the pulse was applied for 40 seconds.

In one example, the method according to any aspect of the present invention may be carried out in an apparatus that is capable of shock wave fragmentation. This apparatus may be selected from that provided by Impulstec (Radebeul, Germany) or Selfrag (Switzerland) or the like. More in particular, the apparatus may be Impulstec EHF-400 or SELFRAG Lab.

Since the method according to any aspect of the present invention does not result in the complete destruction of the cell for the target protein and/or lipid to be released, the cells may be reused after step (b) for the next cultivation. In particular, the cell viability after the EHF treatment may be at least about 5%. More in particular, cell viability may be at least about 4, 3, 2 or 1%. The viable cells may then be reused for the next cultivation. Any method known in the art may be used to determine cell viability. In one example, determination of CFU/mL (colony forming units per mL) may be used.

About 20-90% of the target protein and/or lipid may be released from the cell into the aqueous medium according to any aspect of the present invention. In particular, 20-90, 20-85, 20-80, 20-75, 20-70, 20-65, 20-60, 20-55, 20-50, 25-90, 25-85, 25-80, 25-75, 25-70, 25-65, 25-60, 25-55, 25-50, 30-90, 30-85, 30-80, 30-75, 30-70, 30-65, 30-60, 30-55, 30-50, 35-90, 35-85, 35-80, 35-75, 35-70, 35-65, 35-60, 35-55, 35-50, 40-90, 40-85, 40-80, 40-75, 40-70, 40-65, 40-60, 40-55, 40-50, 45-90, 45-85, 45-80, 45-75, 45-70, 45-65, 45-60, 45-55, 45-50, 50-90, 50-85, 50-80, 50-75, 50-70, 50-65, 50-60, 55-90, 55-85, 55-80, 55-75, 55-70, 60-90, 60-85, 60-80, 60-75, 60-70, 65-90, 65-85, 65-80, 65-75, 70-90, 70-85, 70-80, 75-90, 75-85, 75-80% of the target protein and/or lipid found in the cell may be released from the cell into the aqueous medium in the method according to any aspect of the present invention. More in particular, about 90, 85, 80, 75, 70, 65, 60, 55, 50% of the target protein and/or lipid from in the cell may be released into the aqueous medium in the method of cell lysis according to any aspect of the present invention. The percentage of target protein and/or lipid released into the aqueous medium may be measured using any method known in the art. In one example, the percentage of target protein and/or lipid released into the aqueous medium may be measured using the SDS-PAGE densitometric method. In particular, the SDS-PAGE densitometric method is described in Muharram M M, Abdel-Kader M S. Utilization of gel electrophoreses for the quantitative estimation of digestive enzyme papain. Saudi Pharm J. 2017; 25(3):359-364.

In one example, before the cell is subjected to the method according to any aspect of the present invention, the cell may first be washed at least once to get as much culture medium as possible out of the cell pellet.

EXAMPLES

The foregoing describes preferred embodiments, which, as will be understood by those skilled in the art, may be subject to variations or modifications in design, construction or operation without departing from the scope of the claims. These variations, for instance, are intended to be covered by the scope of the claims.

Example 1

15 L of cell suspension of *Saccharomyces cerevisiae* (Omas Ur-Hefe, Fala, Germany) with cell concentration 62.5 g/L and conductivity 150 µS/cm was used for cell lysis by EHF using be Impulstec EHF-400 (Radebeul, Germany) with 1-3 electrodes. The yeast cells were resuspended in cold (4° C.) distilled water. The working voltage was set at 40 kV, the frequency was 1 Hz and the impulse energy set at 600 J. 10, 100 or 1000 pulses/shock waves were applied to the cells. The conductivity of the cell suspension after the cell lysis was 1032 µS/cm as measured using a conductometer. The total released protein was determined using a bicinchoninic acid (BCA) assay from Pierce™ BCA Protein Assay Kit. The standard method provided with the kit was used. 37.1% more total protein was released compared to the mechanical lysate as a benchmark. The biggest protein that was released had a size of about 100 kDa as shown using SDS-PAGE.

Example 2

3 L of cell suspension of *Saccharomyces cerevisiae* with cell concentration 62.5 g/L and conductivity 153 µS/cm was used for cell lysis by EHF using SELFRAG Lab from Selfrag (Switzerland). The yeast cells were resuspended in cold (4° C.) distilled water. The working voltage was set at 130 kV, the impulse energy was set at 1000 J and the frequency was 1 Hz. 7 or 40 pulses/shock waves were applied. The conductivity of the cell suspension after the cell lysis was 1006 µS/cm. The total released protein was determinate by BCA assay. 25.1% more total protein was released compared to the mechanical lysate as a benchmark. biggest protein that was released had a size of about 100 kDa as shown using SDS-PAGE.

Example 3

Measurement of Cell Viability

The cell viability was investigated by the determination of the colony forming units per milliliter (CFU/mL). For this purpose, 1 g of wet biomass was resuspended in 9 mL of 0.9% NaCl solution. The undiluted yeasts and three dilutions (10-2; 104; 10-6) were plated out on Sabouraud (SAB) 4% glucose agar (Carl Roth, Karlsruhe, Germany) for each treatment. In each case 100 µL were plated out linearly. The agar plates were incubated for 48 hours at 30° C. The colony-forming units (CFU) were then counted manually. It was found that 4% of the cells could be recycled in both examples.

The invention claimed is:

1. A method of cell lysis for forming at least one pore in a cell wall and/or cell membrane of a cell in an aqueous medium for release of at least one intracellular target protein and/or lipid from the cell into the aqueous medium, the method comprising:
   (a) subjecting the cell with the at least one intracellular target protein and/or lipid in the aqueous medium to an electrohydraulic comminution; and
   (b) separating the at least one intracellular target protein and/or lipid from the cell,
wherein the electrohydraulic comminution is brought about by means of a pulse current source, the cell in the aqueous medium is subjected to electrical impulse discharges between at least two electrodes of an underwater radio path of a container at an operating voltage in the range from 40-130 kV, an impulse energy of 50 to 1500 J per electrode, a pulse frequency of 1 Hz for 40-1000 seconds, whereby at least one pore is formed in the cell wall and/or cell membrane.

2. The method according to claim 1, wherein the aqueous medium is a medium with a conductivity of less than 400 uS/cm.

3. The method according to claim 1, wherein the aqueous medium is distilled water.

4. The method according to claim 1 wherein the cell is selected from the group consisting of a yeast cell, bacterial cell and plant cell.

5. The method according to claim 1, wherein the cell is a yeast cell.

6. The method according to claim 1, wherein the at least one intracellular target protein released from the cell is 20 kDa to 100 kDa in size.

7. The method according to claim 1, wherein the method is carried out in an apparatus that is capable of shock wave fragmentation.

8. The method according to claim 1, wherein the operating voltage is 40 kV, the pulse frequency is 1 Hz and the pulses were applied for 1000 seconds.

9. The method according to claim 1, wherein the operating voltage is 130 kV, the pulse frequency is 1 Hz and the pulses were applied for 40 seconds.

10. The method according to claim 1, wherein 11 to 300 l of the aqueous medium is present in the container.

11. The method according to claim 1, wherein the at least one intracellular target protein and/or lipid is separated from the cell using at least one physical separation step selected from the group consisting of size exclusion chromatography, hydrophobic interaction chromatography, ion exchange chromatography, free-flow-electrophoresis, affinity chromatography, HPLC, lyophilization, extraction, filtration and centrifugation.

12. The method according to claim 1, wherein the at least one intracellular target lipid is 30 to 85 kDa in size.

13. The method according to claim 1, wherein the cells is reused after step (b).

14. The method according to claim 1, wherein 50-90% of the at least one intracellular target protein and/or lipid is released from the cell.

15. The method according to claim 1, wherein 70-85% of the at least one intracellular target protein and/or lipid is released from the cell.

* * * * *